United States Patent [19]

Williams et al.

[11] Patent Number: 4,711,352
[45] Date of Patent: Dec. 8, 1987

[54] DELICATE INSTRUMENT HOLDER AND PROTECTOR

[75] Inventors: Rodger W. Williams; Charles W. Atwood, both of Nashville, Tenn.

[73] Assignee: Vxtra Corp., Nashville, Tenn.

[21] Appl. No.: 896,335

[22] Filed: Aug. 13, 1986

Related U.S. Application Data

[63] Continuation of Ser. No. 739,216, May 30, 1985, abandoned.

[51] Int. Cl.$^4$ ............................................. B65D 83/10
[52] U.S. Cl. .................................. 206/365; 206/363; 206/480; 206/478; 206/481; 206/588; 206/564
[58] Field of Search ............... 206/363, 373, 365, 366, 206/477, 478, 480, 481, 485, 588, 564, 560

[56] References Cited

U.S. PATENT DOCUMENTS 1,171,896  2/1916  Simpson ............................ 206/373
1,217,357  2/1917  Sparrow ............................ 206/373
1,266,031  5/1918  McCully ........................... 206/363
1,407,792  2/1922  Hatzung ........................... 206/373
1,441,251  1/1923  Steffens ............................ 206/373
3,822,783  7/1974  Mortensen ........................ 206/480

FOREIGN PATENT DOCUMENTS 2333710  12/1975  France ............................. 206/511

Primary Examiner—Joseph Man Fu Moy
Attorney, Agent, or Firm—James Arno; Gregg C. Brown; Benjamin J. Hauptman

[57] ABSTRACT

A device for holding and protecting delicate instruments, such as microsurgical instruments, such as microsurgical instruments, is described. The device to protect delicate features of instruments from damage during shipping, storage, or other forms of handling. The device includes a base or stage on which spacing means and first and second securing means are provided.

5 Claims, 4 Drawing Figures

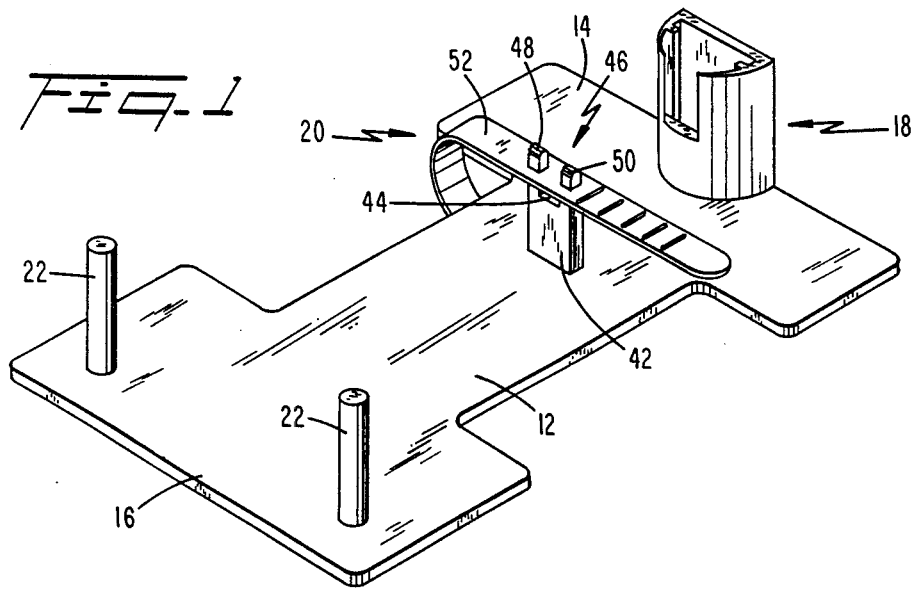
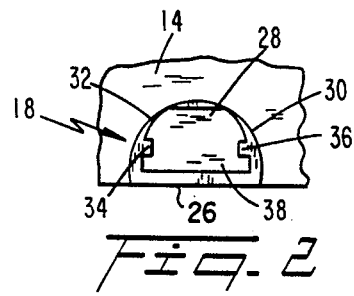
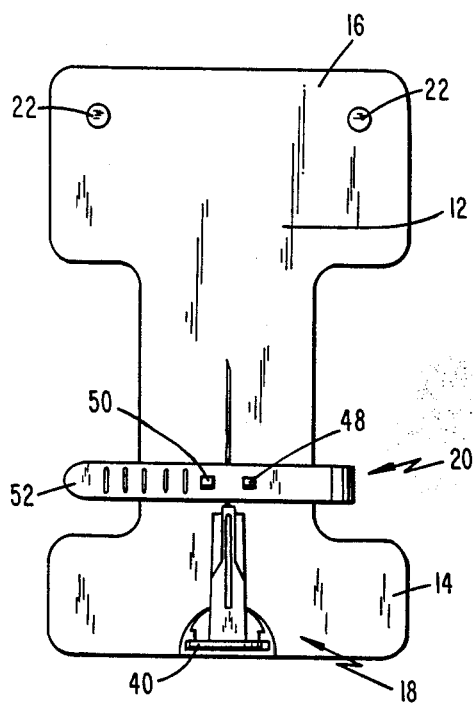
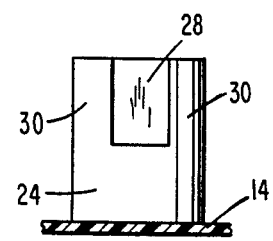

DELICATE INSTRUMENT HOLDER AND PROTECTOR

This application is a continuation of application Ser. No. 739,216, filed May 30, 1985, now abandoned.

BACKGROUND OF THE INVENTION

1. Field of the Invention

The present invention relates to packaging for delicate instruments. More particularly, this invention relates to packaging for surgical instruments that is designed to hold and protect the instruments in a manner such that delicate features of the instruments are not damaged during shipping, storage, or other handling.

2. Discussion of Related Art

A number of sterile, single use surgical instruments have recently been developed. Since such instruments are intended for a single use prior to disposal, it is generally necessary to package the instruments individually in order to maintain the sterility of each instrument prior to use. Thus, the development of disposable surgical instruments has created a need for adjunctive packaging which is specially adapted to meet the requirements of these instruments. In addition, the development of sterile, disposable surgical instruments has created a need for adjunctive packaging which not only maintains the individual sterility of these instruments, but also protects delicate features of the instruments, such as, the cutting blades of microsurgical knives and the tips of microsurgical cannulas.

The present invention is directed toward meeting the above-described specific needs in connection with the packaging of surgical instruments, as well as meeting a more generalized need for the packaging of other types of delicate instruments.

SUMMARY OF THE INVENTION

A principal object of this invention is the provision of packaging for delicate instruments that is designed to hold and protect the instruments in a manner such that fragile features of the instruments are not damaged during shipping, storage, or other handling.

A further object of this invention is the provision of packaging that is specially adapted to hold and protect surgical and microsurgical instruments.

The foregoing objects and other general objectives of the present invention are met by the provision of a device for holding and protecting delicate instruments, comprising a base having a first end portion and a second end portion; first securing means disposed at the first end portion; second securing means disposed between the first securing means and the second end portion; and spacing means disposed between the second securing means and the second end portion.

BRIEF DESCRIPTION OF THE DRAWINGS

The above and still further objects, features, and advantages of the present invention will become apparent upon consideration of the following detailed description of a specific embodiment thereof, especially when taken in conjunction with the accompanying drawings, wherein:

FIG. 1 is an elevated perspective view of an instrument holder and protector according to the present invention;

FIG. 2 is a top plan view of the first securing means;

FIG. 3 is a front view of the first securing means; and

FIG. 4 is a top plan view of the instrument holder and protector shown in FIG. 1 with a needle and needle holder secured thereon.

DESCRIPTION OF THE PREFERRED EMBODIMENTS

Referring to FIGS. 1-4 of the drawings in greater detail, an instrument holder and protector according to the present invention 10 includes: a base 12 having a first end portion 14 and a second end portion 16; first securing means 18 disposed at the first end portion 14; second securing means 20 disposed between the first end portion 14 and second end portion 16; and spacing means 22 disposed between the second securing means 20 and the second end portion 16. The base is designed to provide support for the other components of the instrument holder and protector, and to protect the instrument from forces directed through the base toward the instrument. The base 12 may have various configurations other than the substantially I-shaped, plate-like configuration shown in FIG. 1. The configuration of the base plate is primarily dependent on the shape of the instrument to be mounted on the holder and protector 10.

The first securing means is designed to hold and support one end of an instrument. As best shown in FIGS. 2 and 3, the first securing means 18 is a hollow post 24 having a semi-circular cross section. The post 24 has a flat surface 26 facing away from the second securing means 20, and a slot 28 extending through the upper half of the shaft on the semi-circular surface 30 opposite the flat surface 26. The inner wall 32 of the hollow post 24 is provided with two ridges 34 and 36 disposed opposite each other on the wall. These ridges form a groove 38 located between flat surface 26 and ridges 34 and 36. The groove 38 is adapted to receive and hold an annular ridge 40 on the outer circumference of a needle holder 41 of a microsurgical cannula, as shown in FIG. 4. The first securing means may be designed in a number of other ways to achieve the above-described function. For example, the first securing means may be in the form of a female member designed to hold and support one end of an instrument by mating with a complementary male member present on the instrument or, conversely, the first securing means may be a male member designed for mating with a portion of the instrument which functions as a complementary female member.

The second securing means is designed to hold and support a portion of an instrument opposite from the end held and supported by the first securing means. As shown in FIG. 1, the second securing means 20 includes a support 42 which extends upwardly from base 12. The upper portion of support 42 is provided with a slot 44 to form a generally U-shaped cradle 46 having two prongs 48 and 50. The second securing means 20 further includes a strap 52 which is an integral part of base 12, and is located on a side of the base 12 opposite the support 42. The strap 52 is provided with two holes (not shown) which are adapted to fit over prongs 48 and 50 on support 42, thereby attaching strap 52 to support 42. The second securing means 20 serves to hold and support the needle portion of a needle and needle holder, as shown in FIG. 4, and may hold and support other types of instruments in a similar manner.

The spacing means is designed to protect the instrument from being damaged by the application of pressure in a direction substantially perpendicular to the plane of base 12. That is, the spacing means provides a zone extending upwardly from base 12 which protects the instrument from being crushed or otherwise damaged by forces applied in a direction generally perpendicular to base 10. In the drawings, the spacing means comprises two cylindrical columns disposed at the second end portion 16 of base 12. The columns are substantially the same height as post 24. Although two columns are utilized in the embodiment of the invention illustrated in the drawings, more than two columns can be utilized if desired, and in some cases a single column may be sufficient. The number of columns utilized and the location of the columns between the second securing means 20 and the second end portion 16 are primarily dependent on the nature of the instrument to be protected.

The delicate instrument holder and protector of the present invention may be formed from various types of materials, including wood, metal and plastic. If the holder and protector is intended for use in the packaging of sterile instruments, then it must be formed from a material that is resistant to the effects of sterilization treatments which utilize steam, ethylene oxide, irradiation, microwave energy and/or dry heat.

The holder and protector is preferably formed from polymeric materials using methods known to those skilled in the art. Various types of polymeric materials may be utilized. The polymeric material is preferably one which resists yellowing and is readily moldable. Radiation-resistant homopolymers (e.g., polyethylene, polypropylene, polyethylene thioglycolate and polystyrene) represent the preferred polymeric material. A preferred homopolymer of this type is a commercially available polypropylene polymer manufactured by Himont U.S.A., Inc., Wilmington, Del. and sold under the name PRO-FAX PD 626. Some of the properties of this polymeric material are set forth in the tables below to illustrate typical polymer properties which are desirable in the present invention.

| TYPICAL RESIN PROPERTIES | PRO-FAX PD-626 | ASTM METHOD |
|---|---|---|
| Melt flow rate, dg/min | 12.0 | D 1238 |
| Density, g/cm$^3$ | 0.901 | D 792A-2 |
| Izod impact strength (notched) at 23° C., ft-lbs/in. | 0.8 | D 256A |
| Tensile strength at yield, psi (MPa) | 4,350 (30) | D 638 |
| Flexural modulus, psi (MPa) | 165,000 (1,138) | D 790A |
| Elongation at yield, % | 14.0 | D 638 |
| Deflection temperature at 66 psi, °C. | 80 | D 648 |

| | Before Irradiation | Property Retention After Irradiation$^{(a)}$ | | | |
|---|---|---|---|---|---|
| | | 3 Mrad$^{(b)}$ | | 5 Mrad$^{(b)}$ | |
| | | Initial | 8 Months | Initial | 8 Months |
| Yellowness Index$^{(c)}$ | −.2 | — | +1.3 | — | +1.4 |
| Tensile strength, yield$^{(d)}$ | 5,200 psi | 95% | 95% | 95% | 95% |
| Elongation, ultimate$^{(d)}$ | 375% | 96% | 87% | 96% | 26% |

$^{(a)}$Specimens aged at room temperature after irradiation.
$^{(b)}$Cobalt-60 gamma radiation, dose rate .3 Mrad/hr.
$^{(c)}$40-mil sheet specimen.
$^{(d)}$Determined on 40-mil microtensile specimens.

In the embodiment of the invention illustrated in the drawings, the holder and protector 10 is formed by the injection-molding of polypropylene (PRO-FAX PD 626) and as a result has a single piece construction. Injection molding represents the preferred method of preparing the instrument holder and protector. This preference is based on various factors, such as, uniformity, cost, and physical properties. However, it is possible that other manufacturing methods known to those skilled in the art may be utilized.

While a specific embodiment of the present invention has been described and illustrated, it will be clear that variations of the details of construction which have been specifically illustrated and described may be resorted to without departing from the true spirit and scope of the invention as defined in the appended claims.

What is claimed is:

1. A device for holding and protecting a delicate instrument, comprising a generally rigid base; first means disposed on the base for securing one end of the instrument to the base; second means disposed on the base in spaced relationship from the first securing means for securing another end of the instrument to the base; said first and second securing means arranged to support the instrument in a raised position from the base; and spacing means including at least one spacer column projecting upward from the base to protect the instrument from being damaged by the application of pressure in a direction substantially perpendicular to the base, said second securing means including an opening loosely receiving said another end of the instrument, and means for preventing said another end of the instrument loosely positioned within said opening from being inadvertently dislodged from said opening.

2. The device of claim 1, wherein said delicate instrument is a microsurgical cannula including a needle holder and a needle projecting outwardly therefrom, said needle being loosely received within said opening and thereby having a diameter smaller than the dimension of said opening.

3. A device for holding and projecting a delicate instrument, comprising a base having a first end portion and a second end portion; first means disposed at the first end portion for securing one end of the instrument to the base; second means disposed between the first securing means and the second end portion for securing another end of the instrument to the base; and spacing means disposed between the second securing means and the second end portion, wherein the first securing means includes a hollow post having a slot in the upper portion thereof opposite from the second securing means, the second securing means includes a support located opposite the first securing means, said support having a slot in an upper portion thereof and a prong on each side of the slot, said second securing means further comprising a strap attached to one side of the base opposite the support, said strap having two holes adapted to fit over the prongs on the support to attach the strap to the support, and the spacing means includes at least one column substantially perpendicular to the base.

4. The device of claim 3, wherein the inner wall of the hollow post includes two vertically extending ridges on opposite sides thereof, said ridges forming a groove within the post that is open toward the second securing means.

5. The device of claim 3, wherein said delicate instrument is a needle holder having an annular ridge at one end thereof received within the slot of the hollow post in interfitting engagement, the opposite end of the needle holder containing a needle received within the slot of the support and secured thereto by means of the strap.

* * * * *